United States Patent
Sundermann et al.

(10) Patent No.: US 7,317,034 B2
(45) Date of Patent: Jan. 8, 2008

(54) SUBSTITUTED C-FURAN-2-YL-METHYLAMINE AND C-THIOPHEN-2-YL-METHYLAMINE COMPOUNDS

(75) Inventors: Corrina Sundermann, Aachen (DE); Michael Przewosny, Aachen (DE)

(73) Assignee: Gruenenthal GmbH, Aachen (DE)

( * ) Notice: Subject to any disclaimer, the term of this patent is extended or adjusted under 35 U.S.C. 154(b) by 1 day.

(21) Appl. No.: 11/072,962

(22) Filed: Mar. 7, 2005

(65) Prior Publication Data

US 2005/0148550 A1    Jul. 7, 2005

Related U.S. Application Data

(60) Division of application No. 10/717,932, filed on Nov. 21, 2003, now Pat. No. 6,878,740, and a continuation of application No. PCT/EP02/05542, filed on May 21, 2002.

(30) Foreign Application Priority Data

May 22, 2001   (DE) ................ 101 25 145

(51) Int. Cl.
    A61K 31/381   (2006.01)
    A61K 31/4155  (2006.01)
    C07D 333/20   (2006.01)
    C07D 333/38   (2006.01)
    C07D 409/12   (2006.01)
(52) U.S. Cl. ............ 514/406; 514/438; 514/448; 548/372.1; 549/71; 549/76; 549/77
(58) Field of Classification Search .......... 549/71, 549/77, 68, 72, 73, 74, 75, 76; 514/448, 514/438, 406; 548/372.1
See application file for complete search history.

(56) References Cited

U.S. PATENT DOCUMENTS 3,816,457 A    6/1974   Grisar et al.
3,890,445 A    6/1975   Grisar et al.

FOREIGN PATENT DOCUMENTS

WO   WO-0168816 A1   9/2001
WO   WO-0244171 A1   6/2002

OTHER PUBLICATIONS

E.G. Gray et al, "The Isolation of Nerve Endings from Brain: an electron-microscopic study of cell fragments derived by homogenization and centrifugation" *J. Anat.* (1962) 96:79-88.
J.M. Grisar et al, "Hypoglycemic α-Cycloalkylphenylmethyl, Furanalkyl, and Thiophenealkyl Lactamimides", *J. Med. Chem.* (1976), 19(3) 365-369.
K. Heyns et al. *Chemische Berichte* 89:12, pp. 2833-2844 (1956).
K.G. Lewis et al. "Rearrangements In the Furan Series IV—The Reaction Between Furan-2-carbaldehyde and Aniline" *Aust. J. Chem.* (1990) 43:655-663.
P.J. Meier et al. "Medikamentose Schmerztherapie" *Therapetische Umschau*, (1989) Bd. 46, H. 8, pp. 526-536.
T. Obata et al. "Preparation of aminopyrimidines as insecticides and agrochemical fungicides" *Chemical Abstracts* vol. 115 (1991) p. 378.
N.A. Petasis et al. "One-step three-component reaction among organoboronic acids, amines and salicylaldehydes" *Tetrahedron Letters* 42 (2001) pp. 539-542.
P.J. Pauwels et al. "[3H]Batrachotoxinin A 20-α-Benzoate Binding to Sodium Channels in Rat Brain: Characterization and Pharmacological Significance" *Euro. J. Pharm.* (1986) 124:291-298.

*Primary Examiner*—Bernard Dentz
(74) *Attorney, Agent, or Firm*—Crowell & Moring LLP

(57) ABSTRACT

Substituted C-furan-2-yl-methylamine and C-thiophen-2-yl-methylamine compounds, processes for their preparation, medicaments and pharmaceutical compositions containing them, and their use in treatment methods and in the preparation of analgesics, in the preparation of a local anaesthetic, an antiarrhythmic, an antiemetic, a nootropic agent and/or a medicament for the treatment and/or prophylaxis of cardiovascular diseases, urinary incontinence, diarrhea, pruritus and/or inflammations, and/or a medicament for the treatment of depression and/or alcohol and/or drug and/or medicament abuse, and/or a medicament for increasing vigilance.

23 Claims, No Drawings

US 7,317,034 B2

SUBSTITUTED C-FURAN-2-YL-METHYLAMINE AND C-THIOPHEN-2-YL-METHYLAMINE COMPOUNDS

CROSS-REFERENCE TO RELATED APPLICATIONS

This application is a division of application Ser. No. 10/717,932 filed Nov. 21, 2003 now U.S. Pat. No. 6,878,740 which is a continuation of International Patent Application No. PCT/EP02/05542, filed May 21, 2002, designating the United States of America, and published in German as WO 02/094802, the entire disclosure of which is incorporated herein by reference. Priority is claimed based on Federal Republic of Germany Patent Application No. DE 101 25 145.9, filed May 22, 2001.

FIELD OF THE INVENTION

The present invention relates to substituted C-furan-2-yl-methylamine and C-thiophen-2-yl-methylamine compounds to a process for their preparation, to medicaments and pharmaceutical compositions containing them, and to their use in methods of treatment and in the preparation of analgesics, in the preparation of a local anesthetic, an antiarrhythmic, an antiemetic, a nootropic agent and/or a medicament for the treatment, inhibition and/or prophylaxis of cardiovascular diseases, urinary incontinence, diarrhea, pruritus and/or inflammations, and/or a medicament for the treatment of depression and/or alcohol and/or drug and/or medicament abuse, and/or a medicament for increasing vigilance.

BACKGROUND OF THE INVENTION

The treatment of chronic and non-chronic pain is of great importance in medicine. There is a worldwide need for highly effective therapies for the targeted treatment of chronic and non-chronic pain in a manner that is fair to the patient, which is to be understood to mean the successful and satisfactory treatment of pain for the patient.

Conventional opioids such as morphine are highly effective in the therapy of severe to very severe pain. However, their use is limited by the known side-effects, such as, for example, respiratory depression, vomiting, sedation, constipation and the development of tolerance. In addition, they are less effective in neuropathic or incidental pain, from which tumor patients in particular suffer.

Opioids analgesic action operates by binding to receptors in the cell membrane which belong to the family of the so-called G-protein-coupled receptors. In addition to these, there are further receptors and also ion channels which are substantially involved in the system of pain formation and pain transmission, for example the so-called batrachotoxin (BTX) binding site (=binding site 2) of the sodium channel.

SUMMARY OF THE INVENTION

It is an object of the present invention to provide compounds having analgesic activity which are suitable for the therapy of pain—optionally also for the therapy of chronic and neuropathic pain. In addition, those substances should as far as possible exhibit none of the side-effects that usually occur with the use of opioids such as morphine, such as, for example, nausea, vomiting, dependence, respiratory depression or constipation.

The object is achieved by compounds corresponding to formula (I), which have analgesic activity and exhibit a high affinity for the BTX binding site of the sodium channel. The compounds according to the invention are substituted C-furan-2-yl-methylamine and C-thiophen-2-yl-methylamine compounds corresponding to formula (I)

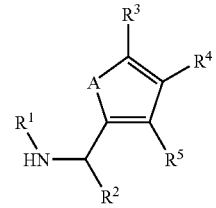

wherein
A represents O or S;
$R^1$ represents aryl, heterocyclyl, —($C_{1-6}$-alkyl)-aryl or —($C_{1-6}$-alkyl)-heterocyclyl;
$R^2$ represents —C(=O)$R^6$ or $C_{3-8}$-cycloalkyl;
$R^3$, $R^4$ and $R^5$ each independently of the others represents H, F, Cl, Br, I, CN, $OR^7$, $SR^8$, $NO_2$, $C_{1-12}$-alkyl, $C_{3-8}$-cycloalkyl, —($C_{1-6}$-alkyl)-$C_{3-8}$-cycloalkyl, aryl, —($C_{1-16}$-alkyl)-aryl, heterocyclyl, —($C_{1-6}$-alkyl)-heterocyclyl, —(CH$^2$)$_m$—O—(CH$_2$)$_n$—$R^9$ wherein m=1, 2, 3 or 4 and n=0, 1, 2, 3 or 4, —(CH$_2$)$_p$—S$_q$—(CH$_2$)$_r$—$R^{10}$ wherein p=1, 2, 3 or 4, q=1 or 2 and r=0, 1, 2, 3 or 4, —(CH$_2$)$_s$—C(=O)OR$^{11}$ wherein s=0, 1, 2, 3 or 4, —C(=O)$R^{12}$ or —C(=S)$R^{13}$;
$R^6$ represents aryl, heterocyclyl, —($C_{1-6}$-alkyl)-aryl or —($C_{1-6}$-alkyl)-heterocyclyl;
$R^7$ and $R^8$ each independently of the other represents H, $C_{1-6}$-alkyl or $C_{3-8}$-cycloalkyl;
$R^9$ and $R^{10}$ each independently of the other represents H, $C_{1-6}$-alkyl, $C_{3-8}$-cycloalkyl, aryl, heterocyclyl or —C(=O)$R^{14}$;
$R^{11}$ represents H, $C_{1-6}$-alkyl or $C_{3-8}$-cycloalkyl;
$R^{12}$ and $R^{13}$ each independently of the other represents $C_{1-6}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl, —($C_{1-6}$-alkyl)-heterocyclyl or —NR$^{15}$R$^{16}$;
$R^{14}$ represents $C_{1-6}$-alkyl, $C_{3-8}$-cycloalkyl, —($C_{1-6}$-alkyl)-$C_{3-8}$-cycloalkyl, aryl or —($C_{1-6}$-alkyl)-aryl; and
$R^{15}$ and $R^{16}$ each independently of the other represents H, $C_{1-8}$-alkyl, $C_{3-8}$-cycloalkyl, —($C_{1-6}$-alkyl)-$C_{3-8}$-cycloalkyl, aryl, —($C_{1-6}$-alkyl)-aryl, heterocyclyl or —($C_{1-6}$-alkyl)-heterocyclyl, or
—NR$^{15}$R$^{16}$ together form a heterocyclyl ring;

in the form of their racemates, in the form of the pure enantiomers or diastereoisomers, or in the form of mixtures of the enantiomers or diastereoisomers in any desired mixing ratio;

with the exception of N-(cyclopropyl-2-thienylmethyl)-4,5-dihydro-2-oxazoleamine and N-(cyclopropyl-2-furanylmethyl)-4,5-dihydro-2-oxazoleamine.

The following racemates of compounds corresponding to formula (I) are described as such in the prior art, without their use in a medicament or in the preparation of a medicament of any kind being disclosed:

1,2-di-2-furanyl-2-(phenylamino)-ethanone (K. G. Lewis and C. E. Mulquiney, *Aust. J. Chem.* (1990), 655-663);

1,2-di-2-furanyl-2-[(4-methylphenyl)amino]-ethanone (K. Heyms and W. Stumme, *Chem. Ber.* (1956) 2833-2844);

1,2-di-2-furanyl-2-(pyrazinylamino)-ethanone;

5-chloro-N-[cyclopropyl[5-(2-ethoxyethyl)-2-thienyl]methyl]-6-ethyl-4-pyridineamine and 5-chloro-N-[cyclopropyl[5-(2-ethoxyethyl)-2-thienyl]methyl]-6-methyl-4-pyridineamine (*Chemical Abstract* 115, 273468).

The present invention accordingly also provides those compounds in so far as processes according to the invention for their preparation, medicaments and pharmaceutical compositions containing them and their use in treatment methods and in the preparation of an analgesic, in the preparation of a local anesthetic, an antiarrhythmic, an antiemetic, a nootropic agent and/or a medicament for the treatment and/or prophylaxis of cardiovascular diseases, urinary incontinence, diarrhea, pruritus and/or inflammations, and/or a medicament for the treatment of depression and/or alcohol and/or drug and/or medicament abuse, and/or a medicament for increasing vigilance are concerned.

Also described in the prior art are the following racemates of compounds corresponding to formula (I) and their use as medicaments or in the preparation of medicaments:

N-(cyclopropyl-2-thienylmethyl)-3,4,5,6-tetrahydro-2-pyridineamine,

N-(cyclopropyl-2-thienylmethyl)-3,4,5,6-tetrahydro-2H-azepineamine and

N-(cyclopropyl-2-thienylmethyl)-3,4,5,6-tetrahydro-2-azocineamine (U.S. Pat. No. 3,890,445; U.S. Pat. No. 3,816, 457; J. M. Grisar et al., *J. Med. Chem.* (1976) 365-369).

The present invention accordingly also provides those compounds in so far as processes according to the invention for their preparation and their use in treatment methods and in the preparation of an analgesic, in the preparation of a local anesthetic, an antiarrhythmic, an antiemetic, a nootropic agent and/or a medicament for the treatment and/or prophylaxis of cardiovascular diseases, urinary incontinence, diarrhea, pruritus and/or inflammations, and/or a medicament for the treatment of depression and/or alcohol and/or drug and/or medicament abuse, and/or a medicament for increasing vigilance are concerned.

Within the scope of this invention the terms "alkyl", "$C_{1-12}$-alkyl", "$C_{1-8}$-alkyl" and "$C_{1-6}$-alkyl" include acyclic saturated or unsaturated hydrocarbon radicals which may be branched or straight-chain and may be unsubstituted or monosubstituted or polysubstituted by identical or different substituents, having (as in the case of $C_{1-12}$-alkyl) from 1 to 12 (i.e. 1, 2, 3, 4, 5, 6, 7, 8, 9, 10, 11 or 12) carbon atoms, having (as in the case of $C_{1-8}$-alkyl) from 1 to 8 (i.e. 1, 2, 3, 4, 5, 6, 7 or 8) carbon atoms or having (as in the case of $C_{1-6}$-alkyl) from 1 to 6 (i.e. 1, 2, 3, 4, 5 or 6) carbon atoms, i.e. $C_{1-12}$-alkanyls, $C_{1-8}$-alkanyls and $C_{1-6}$-alkanyls, $C_{2-12}$-alkenyls, $C_{2-8}$-alkenyls and $C_{2-6}$-alkenyls, and $C_{2-12}$-alkynyls, $C_{2-8}$-alkynyls and $C_{2-6}$-alkynyls. "Alkenyls" have at least one C—C double bond and "alkynyls" have at least one C—C triple bond, while "alkanyls" are saturated. Alkyl is advantageously alkanyl and is selected from the group comprising methyl, ethyl, n-propyl, 2-propyl, n-butyl and tert.-butyl.

Within the scope of this invention "$C_{3-8}$-cycloalkyl" (or "cycloalkyl") denotes a cyclic saturated or unsaturated hydrocarbon radical having 3, 4, 5, 6, 7 or 8 carbon atoms, wherein the radical may be unsubstituted or monosubstituted or polysubstituted by identical or different substituents and may optionally be benzo-fused. Cycloalkyl is, for example, cyclopropyl, cyclobutyl, cyclopentyl, cyclohexyl, cycloheptyl, cyclooctyl, cyclopentenyl, cyclohexenyl, cycloheptenyl and cyclooctenyl. For the purposes of the present invention, particular preference is given to cyclopropyl, cyclopropyl-2-carboxylic acid and cyclopropyl-2-carboxylic acid ethyl ester. The optionally substituted cyclopropyl radical is also designated cyclo-$C_3H_5$.

For the purposes of the present invention the term "aryl" is understood to be a radical which is selected from the group comprising phenyl, naphthyl, anthracenyl and biphenyl and which is unsubstituted or monosubstituted or polysubstituted by identical or different substituents. It is also possible for the aryl radicals to be fused with further saturated, (partially) unsaturated or aromatic ring systems. Each aryl radical may be unsubstituted or mono- or polysubstituted, it being possible for the aryl substituents to be identical or different and to be at any desired position of the aryl. Aryl is advantageously a phenyl radical that is unsubstituted or monosubstituted or polysubstituted by identical or different substituents.

The term "heterocyclyl" denotes a monocyclic or polycyclic organic radical in which at least one ring contains one hetero atom or 2, 3, 4 or 5 identical or different hetero atoms selected from the group comprising N, O and S, the radical being saturated or unsaturated and unsubstituted or monosubstituted or polysubstituted by identical or different substituents. Examples of heterocyclyl radicals within the scope of this invention include monocyclic five-, six- or seven-membered organic radicals having one hetero atom or 2, 3, 4 or 5 identical or different hetero atoms which are nitrogen, oxygen and/or sulfur, and their benzo-fused analogues. A sub-group of the heterocyclyl radicals is formed by the "heteroaryl" radicals, which are heterocyclyl radicals in which the hetero-atom-containing ring, of which there is at least one, is heteroaromatic. Each heteroaryl radical may be unsubstituted or monosubstituted or polysubstituted by identical or different substituents. Examples of heterocyclyl radicals within the scope of the present invention include pyrrolidinyl, tetrahydrofuryl, piperidinyl, piperazinyl and, especially, morpholinyl. Examples of heterocyclyl radicals which at the same time are heteroaryl radicals include pyrrolyl, imidazolyl, pyridazinyl, pyrimidinyl, pyrazinyl, furanyl, thienyl, pyridinyl and, especially, pyrazolyl and their benzo-fused analogues. All those radicals may each be unsubstituted or monosubstituted or polysubstituted by identical or different substituents. When —$NR^{15}R^{16}$ together form a heterocyclyl ring, that ring is preferably a pyrrolidinyl, piperidinyl, piperazinyl or morpholinyl radical.

For the purposes of the present invention the terms "($C_{1-6}$-alkyl)-$C_{3-8}$-cycloalkyl", "($C_{1-6}$-alkyl)-heterocyclyl" and "($C_{1-6}$-alkyl)-aryl" mean that the cycloalkyl, heterocyclyl or aryl radical is bonded by way of a $C_{1-6}$-alkyl group to the compound substituted thereby.

Within the scope of this invention the term "substituted" in connection with "alkyl", "alkanyl", "alkenyl", "alkynyl" and "cycloalkyl" is understood to mean the substitution of a hydrogen atom by, for example, F, Cl, Br, I, —CN, —NC, $NH_2$, NH-alkyl, NH-aryl, NH-alkyl-aryl, NH-heterocyclyl, NH-alkyl-OH, N(alkyl)$_2$, N(alkyl-aryl)$_2$, N(heterocyclyl)$_2$, N(alkyl-OH)$_2$, NO, $NO_2$, SH, S-alkyl, S-aryl, S-alkyl-aryl, S-heterocyclyl, S-alkyl-OH, S-alkyl-SH, OH, O-alkyl, O-aryl, O-alkyl-aryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heterocyclyl, C(=S)-heterocyclyl, $CO_2$H, $CO_2$-alkyl, $CO_2$-alkyl-aryl, C(=O)$NH_2$, C(=O)NH-alkyl, C(=O)NHaryl, C(=O)NH-heterocyclyl, C(=O)N(alkyl)$_2$, C(=O)N(alkyl-aryl)$_2$, C(=O)N(heterocyclyl)$_2$, SO-alkyl, $SO_2$-alkyl, $SO_2$-alkyl-aryl, $SO_2NH_2$, $SO_3$H, $SO_3$-alkyl, cycloalkyl, aryl or by heterocyclyl, polysubstituted radicals being understood to be radicals that are polysubstituted, for example di- or tri-substituted, either at different atoms or at the same atom, for example trisubstituted at the same carbon atom, as in the case of $CF_3$ or —$CH_2CF_3$, or at different positions, as in the case of —CH(OH)—CH=CCl—$CH_2$Cl. Polysubstitution can be carried out with the same or with different substituents. For the purposes of the present invention, particular preference is given to $CF_3$, —$CH_2$—OH and —$CH_2$—C(=O)Oethyl as substituted alkyl and to cyclopropyl-2-carboxylic acid and cyclopropyl-2-carboxylic acid ethyl ester as substituted cycloalkyl.

With regard to "aryl", "heterocyclyl" and "heteroaryl", "monosubstituted" or "polysubstituted" is understood to mean within the scope of this invention the mono- or poly-substitution, for example di-, tri- or tetra-substitution, of one or more hydrogen atoms of the ring system by a suitable substituent. If the meaning of such suitable substituents in connection with "aryl", "heterocyclyl" or "heteroaryl" is not defined elsewhere in the description or in the claims, suitable substituents are F, Cl, Br, I, —CN, —NC, $NH_2$, NH-alkyl, NH-aryl, NH-alkyl-aryl, NH-heterocyclyl, NH-alkyl-OH, $N(alkyl)_2$, $N(alkyl-aryl)_2$, $N(heterocyclyl)_2$, $N(alkyl-OH)_2$, NO, $NO_2$, SH, S-alkyl, S-cycloalkyl, S-aryl, S-alkyl-aryl, S-heterocyclyl, S-alkyl-OH, S-alkyl-SH, OH, O-alkyl, O-cycloalkyl, O-aryl, O-alkyl-aryl, O-heterocyclyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heterocyclyl, C(=S)-heterocyclyl, $CO_2$H, $CO_2$-alkyl, $CO_2$-alkyl-aryl, C(=O)$NH_2$, C(=O)NH-alkyl, C(=O)NHaryl, C(=O)NH-heterocyclyl, C(=O)$N(alkyl)_2$, C(=O)$N(alkyl-aryl)_2$, C(=O)N(heterocyclyl)$_2$, S(O)-alkyl, S(O)-aryl, $SO_2$-alkyl, $SO_2$-aryl, $SO_2NH_2$, $SO_3$H, $CF_3$, =O, =S; alkyl, cycloalkyl, aryl and/or heterocyclyl; at one atom or optionally at different atoms (it being possible for a substituent itself to be substituted). Polysubstitution is carried out with the same or with different substituents.

For the purposes of the present invention "benzo-fused" means that a benzene ring is fused on another ring.

Pharmaceutically acceptable salts within the scope of this invention are those salts of the compounds corresponding to formula (I) according to the invention which are physiologically tolerable when used pharmaceutically—especially when used in mammals and/or humans. Such pharmaceutically acceptable salts can be formed, for example, with inorganic or organic acids or, where the compounds according to the invention are carboxylic acids, with bases.

The pharmaceutically acceptable salts of the compounds corresponding to formula (I) according to the invention are preferably formed with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. If the compounds according to the invention are carboxylic acids, the pharmaceutically acceptable salts can also be formed by reaction with bases, such as, for example, sodium hydrogen carbonate or sodium carbonate. The salts formed are, inter alia, hydrochlorides, hydrobromides, phosphates, carbonates, hydrogen carbonates, formates, acetates, oxalates, succinates, tartrates, fumarates, citrates and glutamates, or sodium salts. Also preferred are the hydrates of the compounds according to the invention, which can be obtained, for example, by crystallization from aqueous solution.

All the compounds according to the invention contain at least one center of asymmetry, namely the $R^2$- and NH—$R^1$-substituted carbon atom of formula (I). Accordingly, the compounds corresponding to formula (I) according to the invention can be in the form of their racemates, in the form of the pure enantiomers and/or diastereoisomers or in the form of mixtures of those enantiomers or diastereoisomers, both in substance and in the form of pharmaceutically acceptable salts of those compounds. The mixtures may be present in any desired mixing ratio of the stereoisomers. The compounds corresponding to formula (I) are preferably in the form of enantiomerically pure compounds.

Preference is given to compounds corresponding to formula (I) wherein
$R^1$ represents aryl or heterocyclyl;
$R^2$ represents —(C=O)$R^6$ or $C_{3-6}$-cycloalkyl;
$R^3$, $R^4$ and $R^5$ each independently of the others represents H, $C_{1-6}$-alkyl, —$(CH_2)_m$—O—$R^9$ wherein m=1 or 2, —$(CH^2)_p$—$S_q$—$(CH_2)_r$—$R^{10}$ wherein p=1 or 2, q=1 and r=0, 1 or 2, —$(CH_2)_s$—C(=O)O$R^{11}$ wherein s=0, 1 or 2;
$R^6$ represents aryl or heterocyclyl;
$R^9$ and $R^{10}$ each independently of the other represents H, $C_{1-6}$-alkyl or heterocyclyl; and
$R^{11}$ represents H or $C_{1-6}$-alkyl.

Particular preference is given to compounds corresponding to formula (I) wherein
$R^1$ represents aryl$^1$ or heterocyclyl$^1$;
$R^2$ represents —(C=O)-phenyl or -cyclo-$C_3H_4R^{17}$;
$R^3$, $R^4$ and $R^5$ each independently of the others represents H, methyl, —$CH_2$—OH, —$CH_2$—S—$CH_3$ or —$CH_2$—S—$CH_2$-furan-2-yl, —C(=O)Omethyl, —C(=O)Oethyl, —$CH_2$—C(=O)Oethyl;

aryl$^1$ represents

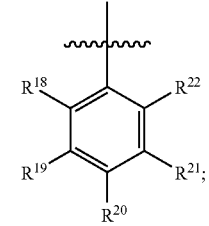

heterocyclyl$^1$ represents

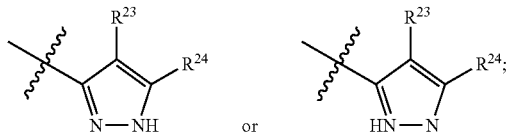

$R^{17}$ represents —C(=O)OH or —C(=O)O—$C_{1-6}$-alkyl; and
$R^{18}$, $R^{19}$, $R^{20}$, $R^{21}$, $R^{22}$, $R^{23}$ and $R^{24}$ each independently of the others represents H, OH, SH, —O—$C_{1-6}$-alkyl, —Oaryl, —S—$C_{1-6}$-alkyl, —Saryl, F, Cl, Br, I, —CN, $C_{1-6}$-alkyl, $CF_3$, CO(=O)H, CO(=O)—$C_{1-6}$-alkyl or —N=N-aryl.

Of those, very particular preference is given to those compounds corresponding to formula (I) wherein
$R^2$ represents —(C=O)-phenyl or -cyclo-$C_3H_4$—C(=O)Oethyl;

R³ represents H, methyl, —CH₂—S—CH₃, —CH₂—S—CH₂-furan-2-yl or —CH₂—C(=O)Oethyl;

R⁴ represents H, methyl, —CH₂—OH, —C(=O)Omethyl or —C(=O)Oethyl;

R⁵ represents H;

R¹⁸, R¹⁹, R²⁰, R²¹ and R²² each independently of the others represents H, —Ophenyl, F, Cl, Br, —CN, methyl or CF₃, wherein at least three of the radicals R¹⁸, R¹⁹, R²⁰, R²¹ and R²² represent H; and R²³ and R²⁴ each independently of the other represents H, OH, —S-methyl, —CN, CO(=O)-ethyl or —N=N-phenyl.

Examples of advantageous compounds of the present invention are selected from the group comprising 5-[1-(2-chloro-phenylamino)-2-oxo-2-phenyl-ethyl]-2-methyl-furan-3-carboxylic acid ethyl ester;

5-[1-(4-chloro-2-methyl-phenylamino)-2-oxo-2-phenyl-ethyl]-2-methyl-furan-3-carboxylic acid methyl ester;

5-[1-(4-chloro-2-fluoro-phenylamino)-2-oxo-2-phenyl-ethyl]-2-methyl-furan-3-carboxylic acid methyl ester; and 5-[1-(4-chloro-2-methyl-phenylamino)-2-oxo-2-phenyl-ethyl]-2-methyl-furan-3-carboxylic acid ethyl ester;

and their pharmaceutically acceptable salts, especially their hydrochlorides.

The present invention relates also to a process for the preparation of a compound corresponding to formula (I) as defined above, wherein an amine corresponding to formula (II)

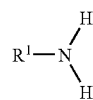

II wherein R¹ is as defined above, is reacted in the presence of an acid with an aldehyde corresponding to formula (III)

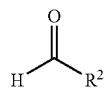

III wherein R² is as defined above, and with a heterocycle corresponding to formula (IV)

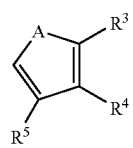

IV wherein A, R³, R⁴ and R⁵ are as defined above.

The acid used is an inorganic or organic protonic or Lewis acid. The reaction is preferably carried out in the presence of an organic acid, for example acetic acid, trifluoroacetic acid or methanesulfonic acid, especially trifluoroacetic acid.

The preparation process according to the invention can be carried out in any suitable solvent in which the reactants are sufficiently soluble. Preferred solvents are organic solvents, for example dichloromethane and, especially, acetonitrile.

The processes according to the invention are advantageously carried out at a temperature of from 0 to 100° C., especially at from 15 to 50° C. The reaction time is preferably from 15 minutes to 12 hours and can be adapted to the particular requirements.

All the amines corresponding to structure (II), the aldehydes corresponding to structure (III) and the thiophenes or furans corresponding to structure (IV) used in the processes according to the invention are commercially available or can be prepared according to processes generally known in the art.

The process according to the invention can also be carried out in semi- or fully automated form as the parallel synthesis of a group of compounds corresponding to formula (I) according to the invention, so that it is also readily possible to prepare substance libraries that contain at least one compound and preferably at least 80 and especially 160 compounds corresponding to formula (I) according to the invention (or an integral multiple thereof).

For the purposes of the present invention a "substance library" is understood to be a group of compounds that are prepared by the same process under identical or virtually identical reaction conditions and by varying a reagent or a plurality of reagents. Such a substance library can contain the library members both in the form of individual pure compounds and in the form of a mixture of those compounds. With the aid of such a substance library it is possible, for example, to carry out medical screening in automated form in one or more in vitro screening processes.

The compounds corresponding to formula (I) according to the invention can be isolated both in substance and in salt form. The substances corresponding to formula (I) are usually obtained after reaction according to the above-described process according to the invention and subsequent conventional working up. The compounds so obtained can then be converted into the corresponding salt, for example by the addition of an inorganic or organic acid, preferably hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed are inter alia hydrochlorides, hydrobromides, phosphates, carbonates, hydrogen carbonates, formates, acetates, oxalates, succinates, tartrates, fumarates, citrates and glutamates. If the compounds corresponding to formula (I) according to the invention are carboxylic acids, the salt formation can be effected by addition of a physiologically tolerable base, for example NaHCO₃ or sodium carbonate; the formation of the sodium salt in particular is preferred for the carboxylic acids. Formation of the hydrochloride, which is particularly preferred, can also be effected especially by addition of trimethylsilyl chloride (TMSCl) to the base (I) dissolved in a suitable organic solvent.

If the compounds corresponding to formula (I) are obtained in the preparation process according to the invention in the form of racemates or in the form of mixtures of their different enantiomers and/or diastereoisomers, such mixtures can be separated by processes which are well known in the art. Suitable methods are, inter alia, chromatographic separation processes, especially liquid chromatography processes under normal or elevated pressure, preferably MPLC and HPLC processes, and also fractional crystallization processes. By means of such processes it is possible especially to separate individual enantiomers from one another, for example by means of HPLC on chiral phase or by means of crystallization of diastereoisomeric salts formed with chiral acids, for example (+)-tartaric acid, (−)-tartaric acid or (+)-10-camphorsulfonic acid, or—where acids are concerned—with chiral bases, for example brucine or (−)-ephedrine.

The invention also provides a medicament or pharmaceutical composition containing at least one compound corresponding to formula (I) according to the invention as defined above or a pharmaceutically acceptable salt thereof. The compounds according to the invention can be present in the medicament according to the invention in the form of isomerically pure compounds, especially enantiomerically pure or diastereoisomerically pure compounds, or in the form of a racemic or non-racemic mixture. The medicament preferably contains a pharmaceutically acceptable salt of the compounds according to the invention, especially a hydrochloride or a sodium salt.

The invention relates also to the use of at least one compound corresponding to formula (I) according to the invention, including their diastereoisomers or enantiomers, also in the form of racemates or a mixture of enantiomers, in the form of their free base or acid or of a salt formed with a physiologically tolerable acid or base, especially in the form of the hydrochloride salt and the sodium salt, in treatment methods or in the preparation of a medicament for the treatment of pain. The compounds according to the invention have proved to have analgesic activity and exhibit a high affinity for binding site 2 of the sodium channel (BTX binding site).

On account of the pronounced binding of the compounds corresponding to formula (I) according to the invention to the BTX binding site, it has also been found that the compounds are suitable also for use in respect of further indications. Accordingly, the present invention relates also to the use of compounds corresponding to formula (I) or of their pharmaceutically acceptable salts in treatment methods or in the preparation of a local anesthetic, an antiarrhythmic, an antiemetic, a nootropic agent and/or a medicament for the treatment and/or prophylaxis of cardiovascular diseases, urinary incontinence, diarrhea, pruritus and/or inflammations, and/or a medicament for the treatment of depression and/or alcohol and/or drug and/or medicament abuse, and/or a medicament for increasing vigilance.

The present invention also provides pharmaceutical compositions that contain at least one compound corresponding to formula (I) as defined above, or a pharmaceutically acceptable salt thereof, and one or more pharmaceutical excipients.

The medicaments and pharmaceutical compositions according to the invention can be in liquid, semi-solid or solid pharmaceutical dosage forms and can be administered in the form of, for example, injectable solutions, drops, juices, syrups, sprays, suspensions, granules, tablets, pellets, transdermal therapeutic systems, capsules, plasters, suppositories, ointments, creams, lotions, gels, emulsions or aerosols, and, in addition to at least one compound corresponding to formula (I) according to the invention, they contain, according to the particular galenical form, pharmaceutical excipients, such as, for example, carriers, fillers, solvents, diluents, surface-active substances, colorings, preservatives, disintegrators, glidants, lubricants, flavorings and/or binders. Such excipients may be, for example: water, ethanol, 2-propanol, glycerol, ethylene glycol, propylene glycol, polyethylene glycol, polypropylene glycol, glucose, fructose, lactose, saccharose, dextrose, molasses, starch, modified starch, gelatin, sorbitol, inositol, mannitol, microcrystalline cellulose, methyl cellulose, carboxymethyl cellulose, cellulose acetate, shellac, cetyl alcohol, polyvinyl-pyrrolidone, paraffins, waxes, natural and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soybean oil, lecithin, sodium lactate, polyoxyethylene and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potassium carbonate, calcium phosphate, dicalcium phosphate, potassium bromide, potassium iodide, talcum, kaolin, pectin, crospovidone, agar and bentonite.

The choice of excipients and the amounts thereof to be used depend on whether the medicament is to be administered by the oral, subcutaneous, parenteral, intravenous, vaginal, pulmonary, intraperitoneal, transdermal, intramuscular, nasal, buccal or rectal route, or locally, for example to the skin, the mucosa or the eyes. For oral administration there are suitable, inter alia, preparations in the form of tablets, dragées, capsules, granules, drops, juices and syrups, and for parenteral and topical administration and for administration by inhalation there are suitable solutions, suspensions, readily reconstitutable powders for inhalation, and also sprays. Compounds corresponding to formula (I) according to the invention in a depot formulation in dissolved form or in a plaster, optionally with the addition of agents promoting penetration of the skin, are suitable preparations for percutaneous administration. Forms of preparation for rectal, transmucosal, parenteral, oral or percutaneous administration may release the compounds corresponding to formula (I) according to the invention in a delayed manner.

The medicaments and pharmaceutical compositions according to the invention are prepared by means, devices, methods and processes which are well known in the art of pharmaceutical formulation, as are described, for example, in "Remington's Pharmaceutical Sciences", ed. A. R. Gennaro, 17th ed., Mack Publishing Company, Easton, Pa. (1985), especially in Part 8, Chapter 76 to 93.

Accordingly, for a solid formulation, for example, such as a tablet, the active ingredient of the medicament, i.e., a compound corresponding to formula (I) or a pharmaceutically acceptable salt thereof, can be granulated with a pharmaceutical carrier, for example conventional tablet constituents such as maize starch, lactose, saccharose, sorbitol, talcum, magnesium stearate, dicalcium phosphate or pharmaceutically acceptable gums, and pharmaceutical diluents, such as, for example, water, in order to form a solid composition which contains a compound according to the invention or a pharmaceutically acceptable salt thereof in homogeneous distribution. Homogeneous distribution is here understood to mean that the active ingredient is distributed evenly throughout the entire composition, so that the latter can readily be divided into unit dose forms, such as tablets, pills or capsules, which each have the same effectiveness. The solid composition is then divided into unit dose forms. It is also possible for the tablets or pills of the medicament according to the invention or of the compositions according to the invention to be coated or otherwise compounded, in order to prepare a delayed-release dosage form. Suitable coating agents are, inter alia, polymeric acids and mixtures of polymeric acids with materials such as, for example, shellac, cetyl alcohol and/or cellulose acetate.

The amount of active ingredient to be administered to the patient varies and is dependent on the weight, the age and the history of past disease in the patient, and also on the mode of administration, the indication and the severity of the disease. Normally, from 0.1 to 5000 mg/kg, especially from 1 to 500 mg/kg, preferably from 2 to 250 mg/kg body weight of at least one compound of the general formula (I) according to the invention are administered.

The Examples which follow serve to illustrate the present invention in greater detail. These Examples are not intended to, and should not be interpreted to limit the scope of the invention or the claims appended hereto.

The automatic synthesis ensures that all samples are treated equally and that the reaction procedure is highly constant.

Some examples of compounds are shown in Table 1:

TABLE 1

| Example | Name | Mass calculated | Mass found |
|---|---|---|---|
| A | 5-[1-(2-Chloro-phenylamino)-2-oxo-2-phenyl-ethyl]-2-methyl-furan-3-carboxylic acid ethyl ester | 383.83 | 384.0/386.1 |
| B | 5-[1-(4-Chloro-2-methyl-phenylamino)-2-oxo-2-phenyl-ethyl]-2-methyl-furan-3-carboxylic acid methyl ester | 397.85 | 398.1/400.2 |
| C | 5-[1-(4-Chloro-2-fluoro-phenylamino)-2-oxo-2-phenyl-ethyl]-2-methyl-furan-3-carboxylic acid methyl ester | 401.82 | 400.4/402.5 |
| D | 5-[1-(4-Chloro-2-methyl-phenylamino)-2-oxo-2-phenyl-ethyl]-2-methyl-furan-3-carboxylic acid ethyl ester | 411.88 | 410.3/412.1/414.1 |

EXAMPLES

The chemicals and solvents used were obtained commercially from one of the following suppliers: Acros, Geel; Avocado, Port of Heysham; Aldrich, Deisenhofen; Fluka, Seelze; Lancaster, Mülheim; Maybridge, Tintagel; Merck, Darmstadt; Sigma, Deisenhofen; TCI, Japan; or were prepared according to general processes known in the art.

Thin-layer chromatographic investigations were carried out using HPTLC precoated plates, silica gel 60 F 254, from E. Merck, Darmstadt.

Each sample was analyzed by ESI-MS and/or NMR. Studies by mass spectrometry (ESI-MS) were carried out using a LCQ Classic mass spectrometer from Finnegan. $^1$H-NMR studies of the compounds according to the invention were carried out using a 300 MHz DPX Advance NMR device from Bruker.

General Working Procedure 1 (GWP 1)

A round-bottomed glass test tube (diameter 16 mm, length 125 mm) with a thread was provided with a stirrer by hand and closed in a capper station with a screw lid having a septum. By means of a robot 1, the test tube was placed in a stirring block adjusted to a temperature of 20° C. The following reagents were pipetted in in succession by a robot 2:
1. 1 ml of a solution containing trifluoroacetic acid and the amino component, in each case 0.1M, in acetonitrile
2. 1 ml of a 0.11 M aldehyde solution in acetonitrile
3. 1 ml of a 0.3 M furan/thiophene solution in acetonitrile.

The reaction mixture was stirred for 600 minutes at 40° C. in one of the stirring blocks. The reaction solution was then filtered in a filtration station. The test tube was rinsed twice with 1.5 ml of a 7.5% NaHCO$_3$ solution.

The rack with the samples was placed manually onto a working-up unit. 2 ml of ethyl acetate were added to the reaction mixture in a vortexer, and shaking was carried out. To form the phase boundary, centrifugation was carried out for a short time in a centrifuge. The phase boundary was detected visually and the organic phase was removed by means of a pipette. In the next step, a further 2 ml of ethyl acetate was added to the aqueous phase, followed by shaking, centrifugation and removal of the organic phase by means of a pipette. The combined organic phases were dried over 2.4 g of MgSO$_4$ (granulated). The solvent was removed in a vacuum centrifuge. Each sample was analyzed by ESI-MS and/or NMR.

Pharmacological Studies

Studies of Binding to the Sodium Channel—Binding Site 2 (BTX Binding):

Binding site 2 of the sodium channel is the so-called batrachotoxin (BTX) binding site. The ligand used was [$^3$H]-batrachotoxinin A20 α-benzoate (10 nM in the batch). Those ion channel particles (synaptosomes) were enriched from the rat cerebrocortex according to Gray and Whittaker (E. G. Gray and V. P. Whittaker, *J. Anat.* (1962) 79-88). Non-specific binding is defined as the radioactivity that is measured in the presence of veratridine (0.3 mM in the batch). Incubation was carried out for 120 minutes at 25° C. The assay conditions corresponded to those of the publication of Pauwels, Leysen and Laduron (P. J. Pauwels, J. E. Leysen and P. M. Laduron, *Eur. J. Pharmacol.* (1986) 291-298).

The $K_D$ value for that binding site is 24.63±1.56 nM. (N=2, i.e., mean values±SEM from 2 independent test series carried out in duplicate parallel tests).

The experimental values of the BTX binding for selected exemplary compounds are shown in Table 2:

TABLE 2

| Example | BTX binding (10 μM) |
|---|---|
| C | 57% |
| D | 37% |
| B | 55% |
| A | 40% |

Pharmaceutical Formulation of a Medicament According to the Invention 1 g of the hydrochloride of 5-[1-(4-chloro-2-fluoro-phenylamino)-2-oxo-2-phenyl-ethyl]-2-methyl-furan-3-carboxylic acid methyl ester was dissolved at room temperature in 1 liter of water for injection purposes and then adjusted to isotonic conditions by addition of sodium chloride.

The foregoing description and examples have been set forth merely to illustrate certain embodiments of the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to formula (I), or a pharmaceutically acceptable salt thereof,

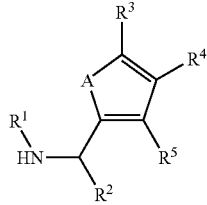

wherein
A represents S;
$R^1$ represents aryl$^1$ or heterocyclyl$^1$;
$R^2$ represents —(C=O)-pheyl or -cyclo -$C_3H_4R^{17}$;
$R^3$, $R^4$ and $R^5$ each independently represent H, methyl, —$CH_2$—OH, —$CH_2$—S—$CH_3$ or —$CH_2$—S—$CH_2$-furan-2-yl, —C(=O)Omethyl, —C(=O)Oethyl, or —$CH_2$—C(=O)Oethyl;
aryl$^1$ represents

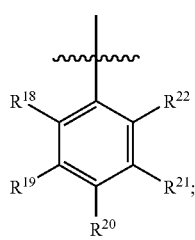

heterocyclyl$^1$ represents

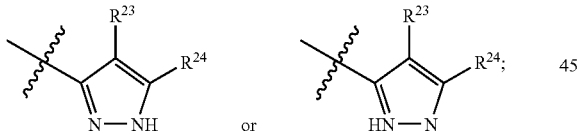

$R^{17}$ represents —C(=O)OH or —C(=O)O—$C_{1-6}$-alkyl; and
$R^{18}$, $R^{19}$, $R^{20}$, $R^{21}$, $R^{22}$, $R^{23}$ and $R^{24}$ each independently represent H, OH, SH, —O—$C_{1-6}$-alkyl, —Oaryl, —S—$C_{1-6}$-alkyl, —Saryl, F, Cl, Br, I, —CN, $C_{1-6}$-alkyl, $CF_3$, CO(=O)H, CO(=O)—$C_{1-6}$-alkyl or —N=N-aryl.

2. The compound of claim 1, wherein said compound is in the form of a racemate.

3. The compound of claim 1, wherein said compound is in the form of a pure enantiomer or diastereoisomer.

4. The compound of claim 1, wherein said compound is in the form of a mixture of enantiomers or diasteroisomers.

5. The compound of claim 1, wherein
$R^2$ represents —(C=O)-phenyl or -cyclo-$C_3H_4$—C(=O)Oethyl;
$R^3$ represents H, methyl, —$CH_2$—S—$CH_3$, —$CH_2$—S—$CH_2$-furan-2-yl or —$CH_2$—C(=O)Oethyl;

$R^4$ represents H, methyl, —$CH_2$—OH, —C(=O)Omethyl or —C(=O)Oethyl;
$R^5$ represents H;
$R^{18}$, $R^{19}$, $R^{20}$, $R^{21}$ and $R^{22}$ each independently represent H, —Ophenyl, F, Cl, Br, —CN, methyl or $CF_3$, wherein at least three of the radicals $R^{18}$, $R^{19}$, $R^{20}$, $R^{21}$ and $R^{22}$ represent H; and
$R^{23}$ and $R^{24}$ each independently represent H, OH, —S-methyl, —CN, CO(=O)-ethyl or —N=N-phenyl.

6. A process for preparing a compound corresponding to formula (I), or a pharmaceutically acceptable salt thereof,

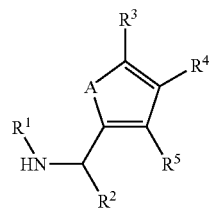

wherein
A represents S;
$R^1$ represents aryl$^1$ or heterocyclyl$^1$;
$R^2$ represents —(C=O)-phenyl or -cyclo -$C_3H_4R^{17}$;
$R^3$, $R^4$ and $R^5$ each independently represent H, methyl, —$CH_2$—OH, —$CH_2$—S—$CH_3$ or —$CH_2$—S—$CH_2$-furan-2-yl, —C(=O)Omethyl, —C(=O)Oethyl, or —$CH_2$—C(=O)Oethyl;
aryl$^1$ represents

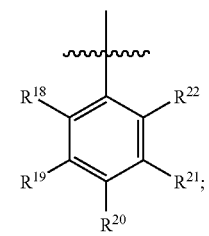

heterocyclyl$^1$ represents

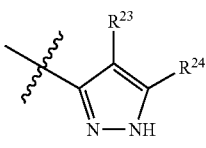 or 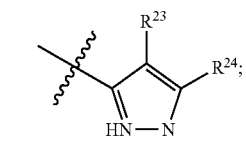

$R^{17}$ represents —C(=O)OH or —C(=O)O—$C_{1-6}$-alkyl; and
$R^{18}$, $R^{19}$, $R^{20}$, $R^{21}$, $R^{22}$, $R^{23}$ and $R^{24}$ each independently represent H, OH, SH, —O—$C_{1-6}$-alkyl, —Oaryl, —S—$C_{1-6}$-alkyl, —S-aryl, F, Cl, Br, I, —CN, $C_{1-6}$-alkyl, $CF_3$, CO(=O)H, CO(=O)—$C_{1-6}$-alkyl or —N=N-aryl;

said process comprising the step of
reacting an amine corresponding to formula (II)

with an aldehyde corresponding to formula (III)

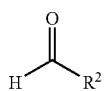

and with a heterocycle corresponding to formula (IV)

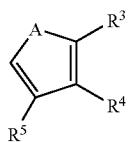

in the presence of an acid.

7. The process of claim 6, wherein the acid is trifluoroacetic acid.

8. The process of claim 6, wherein the step of reacting carried out in an organic solvent and at a temperature of from 0° to 100° C.

9. The process of claim 6, wherein said compound is in the form of a racemate.

10. The process of claim 6, wherein said compound is in the form of a pure enantiomer or diastereoisomer.

11. The process of claim 6, wherein said compound is in the form of a mixture of enantiomers or diasteroisomers.

12. A method of alleviating pain in a mammal, said method comprising administering to said mammal an effective pain alleviating amount of a compound corresponding to formula (I) or a pharmaceutically acceptable salt thereof

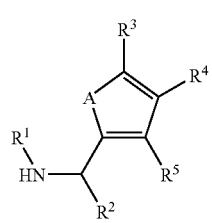

wherein
A represents S;
$R^1$ represents aryl$^1$ or heterocyclyl$^1$;
$R^2$ represents —(C=O)-phenyl or -cyclo-$C_3H_4R^{17}$;
$R^3$, $R^4$ and $R^5$ each independently represent H, methyl, —$CH_2$—OH, —$CH_2$—S—$CH_3$ or —$CH_2$—S—$CH_2$-furan-2-yl, —C(=O)Omethyl, —C(=O)Oethyl, or —$CH_2$—C(=O)Oethyl;

aryl$^1$ represents

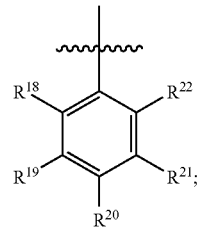

heterocyclyl$^1$ represents

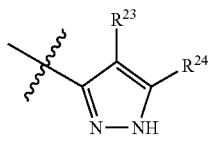 or 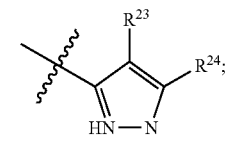

$R^{17}$ represents —C(=O)OH or —C(=O)O—$C_{1-6}$-alkyl; and $R^{18}$, $R^{19}$, $R^{20}$, $R^{21}$, $R^{22}$, $R^{23}$ and $R^{24}$ each independently represent H, OH, SH, —O—$C_{1-6}$-alkyl, —O-aryl, —S—$C_{1-6}$-alkyl, —S-aryl, F, Cl, Br, I, —CN, $C_{1-6}$-alkyl, $CF_3$, CO(=O)H, CO(=O)—$C_{1-6}$-alkyl or —N=N-aryl.

13. The method of claim 12, wherein said compound is in the form of a racemate.

14. The method of claim 12, wherein said compound is in the form of a pure enantiomer or diastereoisomer.

15. The method of claim 12, wherein said compound is in the form of a mixture of enantiomers or diasteroisomers.

16. A method of increasing vigilance or of treating or inhibiting a condition selected from the group consisting of pain, arrhythmia, nausea, cognitive deficit, cardiovascular disease, urinary incontinence, diarrhea, pruritis, inflammation, depression and substance abuse in a mammal, said method comprising administering to said mammal an effective amount of a compound corresponding to formula (I) or a pharmaceutically acceptable salt thereof

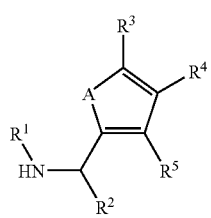

wherein
A represents S;
$R^1$ represents aryl$^1$ or heterocyclyl$^1$;
$R^2$ represents —(C=O)-phenyl or -cyclo $C_3H_4R^{17}$;
$R^3$, $R^4$ and $R^5$ each independently represent H, methyl, —$CH_2$—OH, —$CH_2$—S—$CH_3$ or —$CH_2$—S—$CH_2$-furan-2-yl, —C(=O)Omethyl, —C(=O)Oethyl, or —$CH_2$—C(=O)Oethyl;

aryl¹ represents

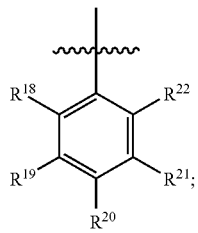

heterocyclyl¹ represents

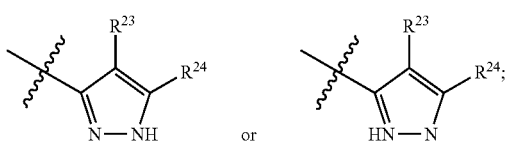

R¹⁷ represents —C(=O)OH or —C(=O)O—$C_{1-6}$-alkyl; and $R^{18}$, $R^{19}$, $R^{20}$, $R^{21}$, $R^{22}$, $R^{23}$ and $R^{24}$ each independently represent H, OH, SH, —O—$C_{1-6}$-alkyl, —O-aryl, —S—$C_{1-6}$-alkyl, —S-aryl, F, Cl, Br, I, —CN, $C_{1-6}$-alkyl, $CF_3$, CO(=O)H, CO(=O)—$C_{1-6}$-alkyl or —N=N-aryl.

17. The method of claim 16, wherein said compound is in the form of a racemate.

18. The method of claim 16, wherein said compound is in the form of a pure enantiomer or diastereoisomer.

19. The method of claim 16, wherein said compound is in the form of a mixture of enantiomers or diasteroisomers.

20. A pharmaceutical composition comprising:
at least one compound corresponding to formula (I) or a pharmaceutically acceptable salt thereof

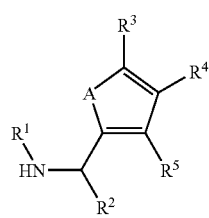

wherein

A represents S;

R¹ represents aryl¹ or heterocyclyl¹;

R² represents —(C=O)-phenyl or -cyclo-$C_3H_4R^{17}$;

$R^3$, $R^4$ and $R^5$ each independently represent H, methyl, —$CH_2$—OH, —$CH_2$—S—$CH_3$ or —$CH_2$—S—$CH_2$-furan-2-yl, —C(=O)Omethyl, —C(=O)Oethyl, or —$CH_2$—C(=O)Oethyl;

aryl¹ represents

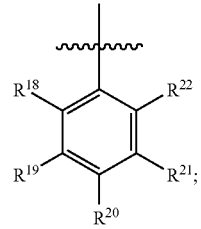

heterocyclyl¹ represents

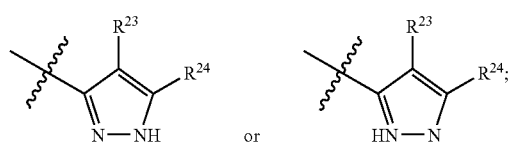

R¹⁷ represents —C(=O)OH or —C(=O)O—$C_{1-6}$-alkyl; and $R^{18}$, $R^{19}$, $R^{20}$, $R^{21}$, $R^{22}$, $R^{23}$ and $R^{24}$ each independently represent H, OH, SH, —O—$C_{1-6}$-alkyl, —O-aryl, —S—$C_{1-6}$-alkyl, —S-aryl, F, Cl, Br, I, —CN, $C_{1-6}$-alkyl, $CF_3$, CO(=O)H, CO(=O)—$C_{1-6}$-alkyl or —N=N-aryl;

and at least one pharmaceutical excipient.

21. The pharmaceutical composition of claim 20, wherein said compound is in the form of a racemate.

22. The pharmaceutical composition of claim 20, wherein said compound is in the form of a pure enantiomer or diastereoisomer.

23. The pharmaceutical composition of claim 20, wherein said compound is in the form of a mixture of enantiomers or diasteroisomers.

* * * * *